(12) United States Patent
Fischer et al.

(10) Patent No.: US 6,948,636 B1
(45) Date of Patent: Sep. 27, 2005

(54) DEVICE FOR ADMINISTERING LIQUIDS

(75) Inventors: Wilfried Fischer, Haan (DE); Matthias Brücker, Gossau (CH)

(73) Assignee: Onkoworks Gesellschaft fur Herstellung und Vertrieb Onkologischer Spezilpraparate mbH, Haan (DE)

(*) Notice: Subject to any disclaimer, the term of this patent is extended or adjusted under 35 U.S.C. 154(b) by 19 days.

(21) Appl. No.: 10/415,571

(22) PCT Filed: Oct. 31, 2000

(86) PCT No.: PCT/DE00/03837

§ 371 (c)(1),
(2), (4) Date: Aug. 21, 2003

(87) PCT Pub. No.: WO02/36185

PCT Pub. Date: May 10, 2002

(51) Int. Cl.[7] ............................................. B65D 35/28
(52) U.S. Cl. ................. 222/103; 222/153.03; 604/135; 604/214
(58) Field of Search ..................... 222/95, 103, 153.03; 604/134, 135, 214

(56) References Cited

U.S. PATENT DOCUMENTS

| | | | | |
|---|---|---|---|---|
| 4,033,479 A | * | 7/1977 | Fletcher et al. | 222/61 |
| 4,157,771 A | * | 6/1979 | Smith | 222/103 |
| 4,991,743 A | * | 2/1991 | Walker | 222/103 |
| 5,025,953 A | * | 6/1991 | Doundoulakis | 222/23 |
| 5,281,202 A | * | 1/1994 | Weber et al. | 604/132 |
| 6,358,239 B1 | * | 3/2002 | Rake et al. | 604/890.1 |

* cited by examiner

Primary Examiner—Joseph A. Kaufman
(74) Attorney, Agent, or Firm—Herbert Dubno; Andrew Wilford

(57) ABSTRACT

A device for dispensing liquid from a bag has upper and lower casing halves and a closure holding together the casing halves. A pressure piston in the casing can press the bag against the lower casing half. This piston is operated by a rocking lever having an upper end bearing on the upper casing half and a lower end on which the piston is pivoted and a tension spring and flexible element connected between the casing halves and the upper end of the rocking lever and angularly biasing the lever for movement from a generally horizontal position with the piston raised and a tilted position with the piston lowered for applying such a force to the pressure piston that a pressure is generated in the bag that causes the discharge of a constant liquid volume per unit of time.

13 Claims, 3 Drawing Sheets

DEVICE FOR ADMINISTERING LIQUIDS

CROSS REFERENCE TO RELATED APPLICATIONS

This application is the U.S. national phase of PCT application PCT/DE00/03837 filed 31 Oct. 2000 and published 20 May 2002 as WO 02/36185.

FIELD OF THE INVENTION

The present invention is directed to a device for administering liquids, especially infusion solutions.

BACKGROUND OF THE INVENTION

Such devices are known. For instance, one application case of such a device relates to the administering of an infusion solution over a long period of time wherein the infusion solution is to be administered in relatively small amounts over the corresponding period of time. Such a device is also known as an "infusion pump". It ensures that the infusion liquid, which is, for instance, contained in an infusion bag, is conducted to the body of the patient from the infusion bag by means of a tube system.

From German utility model 295 08 249 a device for administering medicinal liquids is known which has a bellows—like container which is filled with the liquid to be administered. This bellows-like container is inserted into a substantially cylindrical casing which is closed by a cap-like lid engaging over the casing wall. In the lid of the casing a compression spring is located which applies a pressure force to the bellows-like container. The lid and the casing wall cooperate with a screwthread so that the bellows-like container is progressively pressurized with progressing screwing of the lid onto the casing and the liquid contained in the container which is to be administered is dispensed in this manner.

It is a disadvantage of this known device that the lid has to be screwed further with progressive exhaustion of the bellows-like container. Accordingly, the administering process does not occur automatically.

OBJECT OF THE INVENTION

It is the object of the present invention to provide a device for administering liquids which, with an automatic function, is adapted to be handled or applied in a comfortable and simple manner and which enables a uniform dosing of the liquid which is to be administered.

SUMMARY OF THE INVENTION

According to the invention this object is achieved by a device comprising the following components:
- a lower casing half,
- an upper casing half which is pivotally connected to the lower casing half,
- a closure holding together the casing halves in a closed condition for the formation of a casing,
- a pressure piston located in the casing for the application of pressure to a bag filled with the liquid to be administered which has been laid between the lower casing half and the pressure piston, and
- a mechanism applying such a force to the pressure piston with closed casing and inserted bag that a pressure is generated within the bag which causes the discharge of a constant liquid volume per time unit over the duration of the administering process.

The inventive solution provides a casing having a lower and an upper casing half which are pivotally or rotatably connected with one another. A closure holds together both casing halves in a closed condition. For inserting a bag containing the liquid (infusion solution) the closure is openable so the upper casing half can be tilted up. After insertion of the bag, the upper casing half is tilted back into the closed condition and then the closure locks both casing halves together. The pressure piston inside the casing applies a force to the filled bag in the closed condition of the casing to discharge liquid from the bag, for instance by means of a hose system connected to the bag. In order that the pressure piston can apply such a force, it is itself applied by a mechanism for the application of pressure in such a manner that a pressure is generated within the bag that causes the discharge of a constant liquid volume per unit of time over the period of time of the administering process. In other words, the flow rate of the liquid through a hose connected to the bag is maintained constant over the administering process.

The inventive idea to use such a mechanism instead of a simple compression spring system for the application of a bag containing the liquid to be administered represents one of the central points of the invention. This mechanism eliminates the following phenomenon: When the bag is full, i.e. when the force to generate a certain pressure has to be not so large, a spring is at its maximum tension or compression. However, when the bag is empty and the force must be very high to generate a certain pressure, the spring is hardly compressed or tensioned. According to the invention the discharge of a constant liquid volume per unit of time is achieved in spite of these spring characteristics.

According to a further development of the invention the mechanism has a lever applying a force to the pressure piston and adapted to be modified in its angular position relative to the pressure piston by a tension spring. Accordingly, the application of the force onto the pressure piston is carried out by a modification of the angular position of the lever that is oriented nearly perpendicular to the plane of the pressure piston when the bag is depleted, while it has a position nearly parallel to the plane of the pressure piston when the bag is completely filled. The angle the lever forms with the plane of the pressure piston increases with progressive depletion of the bag. By this, a uniform build up of pressure in the bag during the administering tine is ensured.

Particularly, the mechanism has preferably a rocking lever supported pivotally at one end and displaceable at the upper casing half and pivotally supporting the pressure piston at the other end, and a tension spring connected to the one end of the rocking lever through a flexible cable. This tension spring biases the rocking lever into a tilting position corresponding to the lowermost position of the pressure piston. If no bag has been inserted into the casing, the pressure piston takes its lowermost position corresponding to the most tilted position of the rocking lever. If a bag is inserted and the casing is closed, the rocking lever is pivoted into a position nearly parallel with respect to the plane of the pressure piston in which the tension spring is most stretched. With progressive depletion of the bag, the tension spring is progressively relaxed and the tilting position of the lever is varied. Simultaneously, by this action the arm of the lever (distance between the point of application of the spring and the pivot point of the piston at the rocking lever) with which the tension spring imparts the force onto the pressure piston is varied. If the bag is full (position of the rocking lever approximately parallel to the pressure piston) the arm of the lever is very short while the arm of the lever is very long if the bag is empty (position of the rocking lever highly inclined). Accordingly, the different force of the spring is compensated by variation of the arm of lever ratios.

Preferably, the flexible cable extends over the upper side of the rocking lever, and the upper side is formed in a predetermined contour, especially in a roof-like manner, wherein the cable, dependent on the angular position of the rocking lever, is turned round differently. With this measure the aim of the invention is even better achieved since the rocking lever functions as an eccentric the contour of which determines the arm of lever ratios. The flexible cable runs over the contour of the upper side of the rocking lever so that the arm of lever is determined by the respective contact point of the cable with the contour (preferably roof-shape).

The tension spring is anchored at the inner side of the upper casing half. Of course, the anchoring point of the tension spring with regard to the one end of the rocking lever at which the tension spring is fastened is located beyond the other end of the rocking lever (pivot connection with the pressure piston). According to the respective case of application, the spring characteristic, the lever ratio, the lever shape etc. have to be determined empirically in order to obtain the appropriate conditions of force.

In order to provide roughly symmetrical conditions, the device preferably has at least two rocking levers acting oppositely with respect to one another with associated oppositely acting tension springs wherein the rocking levers have a common pivot axis at the pressure piston at their respective other ends. According to a further development of this embodiment the device has two rocking levers situated on the inside and acting in one direction and two rocking levers situated on the outside and acting into the opposite direction with corresponding tension springs.

Practically, the rocking levers are displaceable on webs by means of rollers wherein the rollers are rotatably supported in their end position in complementary concave recesses of the upper casing half. Preferably, each rocking lever has a roller on each side. Furthermore, the rollers have a groove in their circumference into which the corresponding guide web for the support of the roller engages. In this manner the roller can roll on the web, and the rocking lever is secured against movements parallel to the rotation axes of the rollers.

The associated tension spring acts upon the upper end of the rocking lever through the flexible cable. The cable is fixed in the upper end portion of the rocking lever, for instance imbedded there through an enlargement at the end of the cable. Accordingly, the tension spring applies a torque onto the rocking lever through the cable in order to bring the lever into the nearly vertical tilted position. This movement pushes down the pressure piston and thus compresses the bag (infusion bag).

Preferably, the casing of the inventive device is flat. An embodiment is especially preferred according to which the casing and the pressure piston are formed approximately rectangularly.

The inventive device, if correspondingly designed as above-cited, can be worn on the body, especially with the assistance of a belt under a pullover etc. Accordingly, the casing has preferably on its backside at least one belt loop through which a belt can be pulled. A high wearing comfort results from the flat and especially rectangular shape.

Practically, the closure is formed in such a manner that it comprises at least one closing tongue mounted on one casing half and engaging over the other casing half during closing and coming into locking engagement with the other casing half. Preferably, a closing tongue is provided on each side.

A preferred embodiment is characterized by the feature that the device cannot be opened without the assistance of a special tool. This prevents undesired manipulations of unauthorized persons, for instance by the patient himself. Accordingly, the closure is formed in such a manner that easy manual opening of the casing is not possible.

The invention rather provides a special apparatus for closing and opening the device of the above-cited kind. This apparatus has a lower stationary support part for the fixation of the device and a bow-like upper part for manual handling which is pivotally connected to the lower support part and includes a portion for pressing against the upper casing half of the device. The apparatus for closing and opening (loading apparatus) functions in such a manner that the empty device is inserted into the apparatus in an open condition. The filled bag is laid into the lower casing half of the device. With the bow-like upper part the upper casing half of the device can be pressed against the lower casing half with a reasonable force until the closure is locked. Then, the device is ready for use.

Preferably, the loading apparatus has at its upper part means for releasing the locking of the at least one closing tongue with the other casing part for opening the device. Preferably, the means for releasing has a wedge-like member moving the closing tongue outwardly which can be manually moved downwardly in order to release the closing tongue (the closing tongues). Then, the upper casing half snaps upwardly so that the device is then open. It can be removed from the loading apparatus and again be provided with a new filled bag.

BRIEF DESCRIPTION OF THE DRAWING

In the following the invention is described by means of an example in connection with the drawing in detail. In the drawing.

SPECIFIC DESCRIPTION

Figure 1:
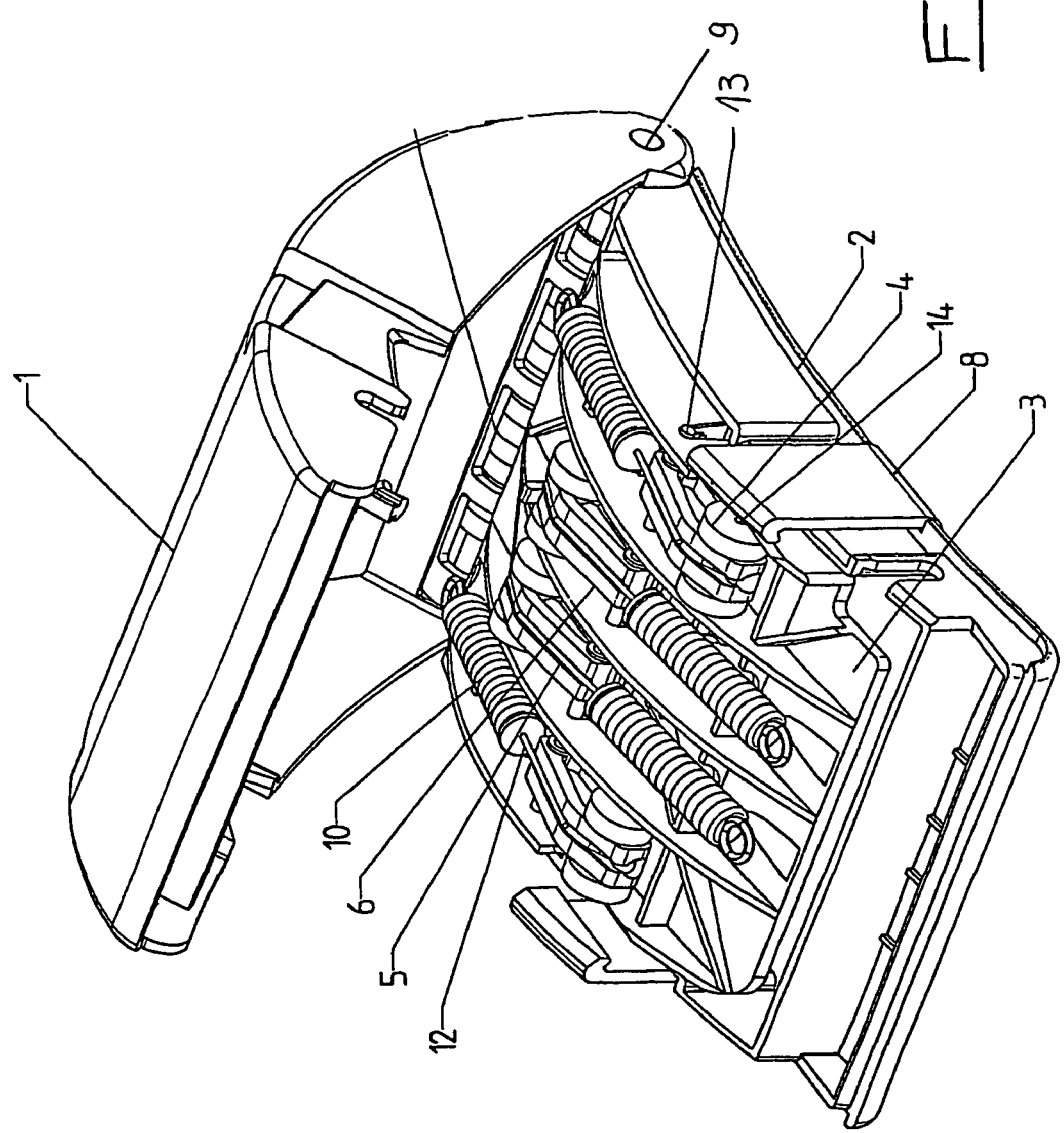
FIG. 1 is a perspective view of a device for administering liquids in an opened condition wherein the springs, tension cables and support for the rocking levers are shown separated from the upper casing half.

As one can see from FIG. 1, the shown device for administering liquids, which, in the present case, is an infusion pump, comprises an upper casing half 1 and a lower casing half 2 which are pivotally connected with one another through a hinge 9. In the closed condition, both halves 1 and 2 form a casing having a flat, generally rectangular shape similar to a buckle or latch. On the back of the lower casing half 2 two belt loops are arranged through which a belt can be pulled with which the infusion pump can be worn on the patient.

When the upper casing half 1 is pivoted closed, two closing tongues 8 laterally mounted on the lower casing half 2 are pushed out somewhat and slide into respective seats in the upper casing half 1 until they finally snap into a corresponding free space and thus lock both casing halves 1 and 2 with one another in a fixed manner. Then, the casing halves cannot be opened easily. To do this, a special apparatus described later is required.

Within the casing a pressure piston 3 is located which has approximately the shape of a rectangle and is formed slightly downwardly concave. The pressure piston 3 is rotatably supported on four rocking levers 6 at an axis of rotation 13 that is arranged generally centrally of the pressure piston 3. The rocking levers are displaceably and rotatably supported at the inner side of the upper casing half. As one can see in FIG. 1, the two inner rocking levers 6 extend from the axis of rotation 13 in FIG. 1 to the right while the two outer rocking levers extend from the axis of rotation 13 in the FIG. to the left. Accordingly, approximately symmetrical conditions are present.

The displaceable and rotatable support of the four rocking levers 6 on the upper casing half 1 is effected with rollers 4, one roller on one end of each rocking lever. These rollers 4 are supported within complementary grooves between inwardly protruding ribs of the inner side of the upper casing half 1. Around their circumference the rollers 4 have central grooves (not shown) which contact corresponding ridges (not shown) on the inner side of the upper casing half 1. The rollers 4 can roll along these ridges.

The rocking levers 6 are connected to tension springs 10 through flexible traction cables 5 so that the tension springs 10 apply tension to the rocking levers 6 at the ends carrying the rollers 4 riding on the inner side of the upper casing half 1. The exact function of the tension springs and rocking levers is explained in connection with FIG. 2.

FIGS. 2*a–f* are perspective sectional views of the device of FIG. 1 for making clear the function of the mechanism for the application of pressure in a stepwise sequence. In each figure only one rocking lever 6 with a tension spring 10 is shown.

Figures 2A, 2B, 2C, 2D, 2E, 2F:
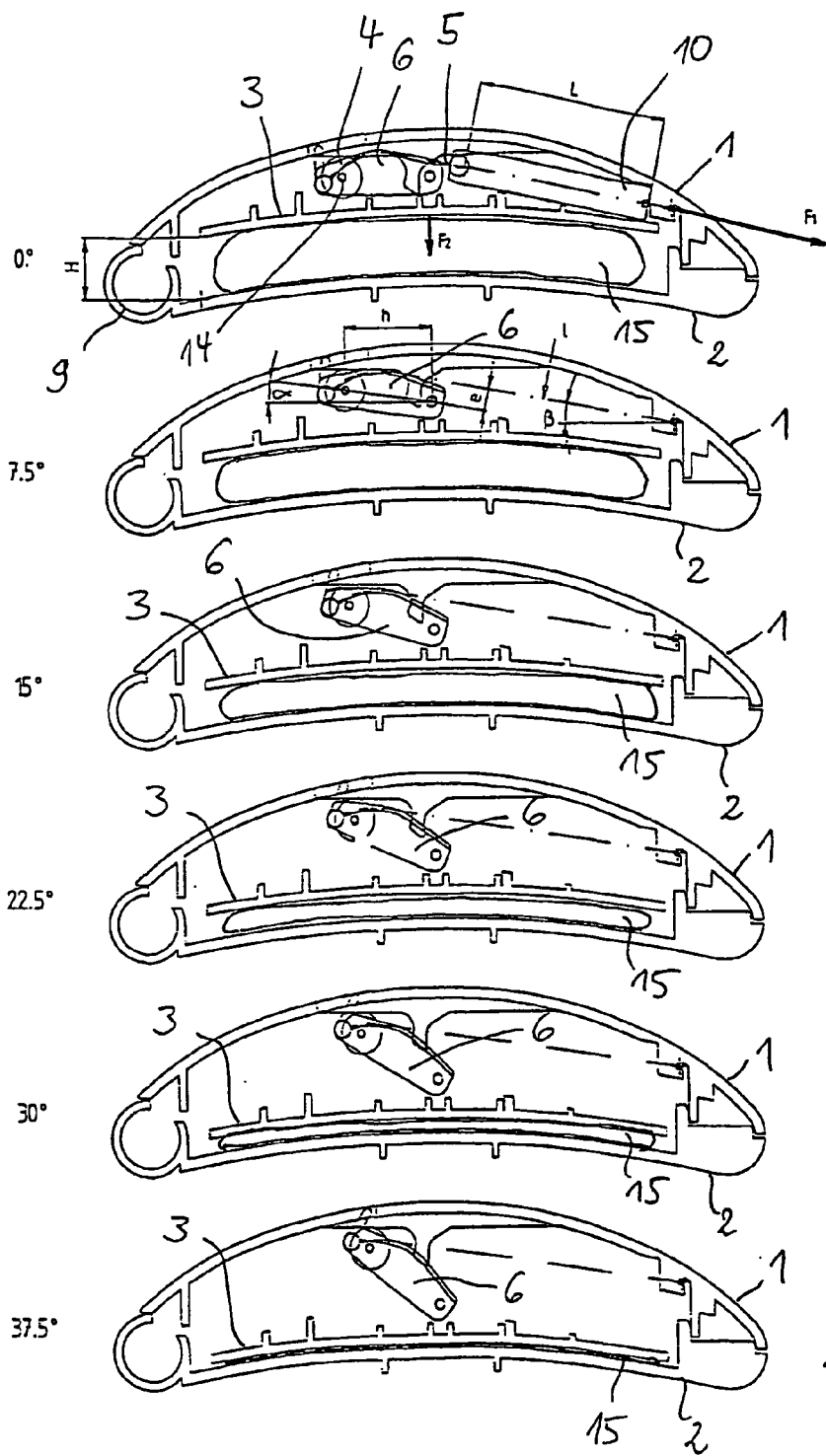
FIGS. 2a–f are perspective sectional views of the device of FIG. 1 showing the function of the mechanism for the application of pressure in a stepwise sequence.

FIG. 2*a* shows the casing consisting of the two casing halves 1 and 2 in the closed condition with an inserted filled infusion solution bag 15. One recognizes that the pressure piston 1 is pressed against the bag 15 with the downwardly directed force F2 by means of the rocking lever 6 whose right-hand end pivotally supports the pressure piston 3. The left end of the rocking lever 6 in the figure rolls on the inner side of the upper casing half 1 by means of the rotatably supported rollers 4 journaled at 14, as above-described in connection with FIG. 1. Each tension spring 10 acts upon this end of the respective rocking lever 6 through a respective flexible traction cable 5. The tension spring 10 has a length L and acts upon the rocking lever 6 with a tension force F1 which is directed to the right in the FIGS. 2*a*–2*f*. The height of the bag 15 is indicated with H.

One recognizes that the rocking lever 6 defines an angle of 0° with the horizontal, i.e. the rocking lever 6 starts in a horizontal position in which the tension spring 10 is most elongated. Furthermore, one can see in FIG. 2*a* that the flexible traction cable 5 passes over the upper side of the rocking lever 6. This upper side is roof-shaped, that is upwardly convex, so that the rocking lever 6 acts as an eccentric and deflects the traction cable 5 fixed to the left end of the rocking lever 6 in the figure. The distance between the contact point of the traction cable 5 and the upper side of the rocking lever 6 on the pressure piston 3 corresponds to the lever arm by means of which the spring force acts upon the pressure piston 3.

FIG. 2*b* shows the bag 15 in an already somewhat depleted position. Here, the pressure piston 3 has already moved down, and the rocking lever 6 takes a position of 7.5° with respect to the horizontal, as indicated with angle α. Furthermore, in FIG. 2*b* the horizontal distance between the pivot points is indicated with h, the distance between the pivot points of the rocking lever 6 on the pressure piston 3 and the contact point of the traction cable 5 (arm of lever) is indicated with e, the direction of tension of the spring 10 is indicated with β, and the length of the spring 10 is indicated with l.

FIGS. 2*c*–2*f* show further steps of the function of the mechanism wherein FIG. 2*f* shows the lowermost position of the pressure piston 3 in which the rocking lever 6 forms an angle of 37.5° with the horizontal. In this position the tension spring 10 is nearly completely detensioned.

Figure 3:
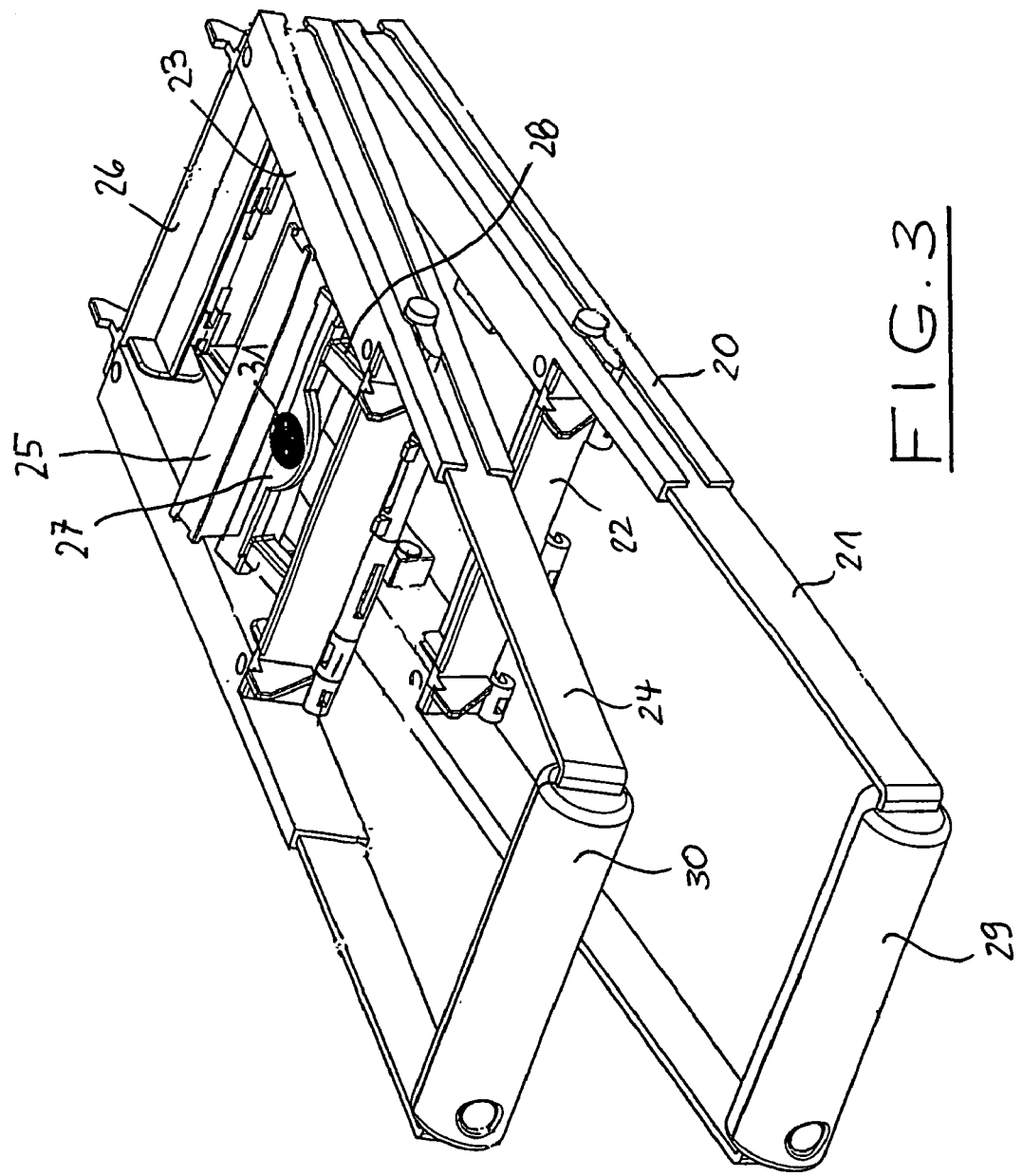
FIG. 3 is a perspective view of a loading apparatus for closing and opening the device shown in FIGS. 1 and 2.

FIG. 3 shows an apparatus for opening and closing the device shown in FIGS. 1 and 2. The apparatus comprises a frame-like lower part 20 having an extensible part 21 with a front grip 29. The frame-like lower part 20 forms the support for the device to be opened or to be closed which can be fixed between the two longitudinal legs as well as the front cross leg 22 and the rear cross leg of the frame-like lower part 20.

The lower support part 20 is pivotally connected to an upper part 23 which is formed like a bow and also has an extensible part 24 at whose front side a handle 30 is located. The two parts 20 and 30 can be extended to an appropriate length by means of the handles 29 and 30. The bow-like upper part 23 is downwardly moved after the insertion of the device which is to be closed such that a crosspiece 25 between the longitudinal legs of the parts 23 and rotatably movably disposed is pressed against the upper side of the upper casing half 1 of the device. In this manner the device is closed.

Furthermore, an opening means 27, i.e. a means for releasing the locking of the closing tongue or tongues with the other casing part 2 of the device, is provided between the longitudinal legs of the upper part 23. This opening means 27 has a crosspiece with a pressing portion indicated at 31 at which the crosspiece is downwardly moved through finger pressure. Wedges 28 are arranged in the two lateral end portions of the crosspiece, so that the wedge-like portions press the closing tongues acting upon the upper casing part 1 of the device to be opened during the downward movement laterally outwardly so that locking between the two casing parts 1 and 2 is released. In this manner, the upper casing part 1 of the device snaps slightly upwardly and can thus be manually opened. Then, the device can be taken from the loading apparatus in order to remove the used bag and to insert a new bag.

In other words, the locking (closing tongue) cannot be released manually since the closing tongue is pressed so strongly into the seat of the upper part 1 of the casing by a very high spring pressure so that the closing tongue, at the existing interior pressure, can be released from the locking position only in a very difficult manner. The loading apparatus serves only to act against this interior pressure by means of the crosspiece 25 and the extensible lever 24 so that the closing tongues can be released from the locking position and the tongues can be pushed to the side with the opening means 27 without overly strong forces.

What is claimed is:

1. A device for administering liquids, the device comprising a lower casing half;

an upper casing half pivotally connected with the lower casing half;

a closure holding together the casing halves in a closed condition for the formation of a casing;

a pressure piston in the casing for applying pressure to a bag between the lower casing half and the pressure piston and filled with the liquid to be administered; and a mechanism having a rocking lever having an upper end bearing on the upper casing half and a lower end on which the piston is pivoted, and a tension spring and flexible element connected between the casing halves and the upper end of the rocking lever and angularly biasing the lever for movement from a generally horizontal position extending generally horizontally with the piston raised and a tilted position with the piston lowered for applying such a force to the pressure piston, when the casing is closed and the bag is laid in, that a pressure is generated in the bag which causes the discharge of a constant liquid volume per unit of time over the period of time of the administering process.

2. The device according to claim 1 wherein the flexible element is a cable passing over the upper side of the rocking lever and the upper side is upwardly convex, whereby the cable, dependent on the angle of position of the rocking lever, is turned round differently.

3. The device according to claim 1, further comprising at least two such rocking levers acting oppositely with respect to one another and having associated oppositely acting respective tension springs, the rocking levers having a common pivot axis at the pressure piston at their respective lower ends.

4. The device according to claim 3, further comprising two inwardly positioned rocking levers acting in one direction and two outwardly positioned rocking levers acting in the opposite direction with corresponding tension springs.

5. The device according to claim 1 wherein the rocking levers are adapted to be displaced on by means of rollers each movable into a respective end position rotatably supported in complementary concave recesses of the upper casing half.

6. The device according to claim 1, further comprising a flat casing.

7. The device according to claim 1 wherein the casing and the pressure piston are formed approximately rectangularly.

8. The device according to claim 1 wherein the pressure piston is concavely formed downwardly in the direction of its longitudinal axis for the adaption to the bag containing the liquid which is to be administered.

9. The device according to claim 1 wherein the casing has at least one belt loop on its backside.

10. The device according to claim 1 wherein the closure has at least one closing tongue located at one casing half, outwardly engaging the other casing half during closing and lockingly engaging the other casing half.

11. An apparatus for closing and opening the device according to claim 1 and comprising a lower stationary support part for the fixation of the device and a bow-like upper part which can be manually handled and which is pivotally connected to the lower support part and has a portion for pressing against the upper casing half of the device.

12. The apparatus according to claim 11 wherein a means for releasing the locking of the at least one closing tongue with the other casing part is provided at the upper part.

13. The apparatus according to claim 12 wherein the means for releasing has a wedge-like member moving the closing tongue outwardly.

* * * * *